(12) United States Patent
Jirathitikal

(10) Patent No.: US 7,384,637 B2
(45) Date of Patent: Jun. 10, 2008

(54) DRUG FOR AIDS TREATMENT

(75) Inventor: Vichai Jirathitikal, Chachoengsao Province (TH)

(73) Assignee: Immunitor USA Inc., College Park, MD (US)

( * ) Notice: Subject to any disclaimer, the term of this patent is extended or adjusted under 35 U.S.C. 154(b) by 861 days.

(21) Appl. No.: 10/118,017

(22) Filed: Apr. 9, 2002

(65) Prior Publication Data

US 2002/0164343 A1   Nov. 7, 2002

Related U.S. Application Data

(62) Division of application No. 09/494,607, filed on Jan. 31, 2000, now abandoned.

(51) Int. Cl.
*A61K 39/21* (2006.01)
(52) U.S. Cl. .................... 424/188.1; 424/208.1
(58) Field of Classification Search .............. 435/5; 424/208.1, 188.1
See application file for complete search history.

(56) References Cited

U.S. PATENT DOCUMENTS

| | | | |
|---|---|---|---|
| 4,921,667 A | 5/1990 | Coico et al. |
| 4,937,071 A | 6/1990 | Cioco et al. |
| 5,525,461 A | 6/1996 | Rittershaus |
| 5,550,166 A | 8/1996 | Ostlund et al. |
| 5,602,305 A | 2/1997 | Pober et al. |
| 5,811,089 A | 9/1998 | Smikodub et al. |
| 5,827,896 A | 10/1998 | Ostlund et al. |
| 5,904,924 A | 5/1999 | Gaynor et al. |

OTHER PUBLICATIONS

Thongcharoen, P., 2004, "V-1 Imunitor", Viral Immunol. 17(3):457.*

V. Jirathitkal et al., Letters to the Editor—Survival of End-Stage Aids Patients Receiving V-1 Immunitor, HIV Clin Trials 2002; 3(3): 258-259.

V. Jirathitkal et al., Safety of Efficacy of an Oral HIV Vaccine (V-1 Immunitor) in Aids Patients at Various Stages of the Disease, HIV Clin Trials 2002;3(1):21-26.

V. Jirathitkal et al., Normalization of Elevated Liver Enzymes Due to V-1 Immunitor Therapy; Electronic Journal of Biotechnology ISSN: 0717-3458, vol. 6, No. 1, pp. 1-4, Issue of Apr. 15, 2003.

V. Jirathitkal et al., V-1 Immunitor: Oral Therapeutic AIDS vaccine with Prophylactic Potential, Vaccine 21 (2003) 624-628.

A. Bourinbaiar et al., Low-Cost Anti-HIV Compounds: Potential Application for Aids Therapy in Developing Countries, Current Pharmaceutical Design, 2003, 9(18): 1419-1431.

V. Jirathitkal et al., Effect of an Oral Therapeutic HIV-1 Vaccine on Aids Patients iwith DC4 Count Above 250 Cells/MM, Acta virologica 48: 73-78 (2004).

V. Jirathitkal et al., Increased Body Weight and Improved Quality of Life in AIDS Patients Following V-1 Immunitor Administration, European Journal of Clinical Nutrition (2004), 58, 110-115.

A. Bourinbaiar et al., Phase II Placebo-Controlled Study of V-1 Immunitor as a Therapeutic Modality for Treatment of HIV, Journal of Clinical Virology, 744 (2004) 1-8.

A. Bourinbaiar et al., Review-Mucosal AIDS Vaccines, Viral Immunology, vol. 16, No. 4 (2003) pp. 427-445.

* cited by examiner

*Primary Examiner*—Jeffrey S. Parkin
(74) *Attorney, Agent, or Firm*—Connolly Bove Lodge & Hutz LLP

(57) ABSTRACT

Raising the T-cell count in an HIV positive patient having a low T-cell count by orally administering an effective amount of a composition containing a material obtained by treating whole human blood or white cells obtained from HIV positive patients with cold aqueous carbon dioxide, heating to evolve carbon dioxide gas, allowing a precipitate to form, and collecting and drying the precipitate.

8 Claims, 1 Drawing Sheet

DRUG FOR AIDS TREATMENT

This application is a Division of application Ser. No. 09/494,607 filed on Jan. 31, 2000 now abandoned

BACKGROUND OF INVENTION

Acquired immune deficiency syndrome, or AIDS, is an infectious disease which weakens the immune system to the point that the body cannot defend itself against diseases and infections that it can normally resist. In some cases, it is these Opportunistic disease, as they are called, that cause the fatalities. AIDS is caused by an infection brought on by the human immune deficiency virus (HIV) that scientists have identified as a retrovirus.

In the immune system of healthy people, white blood cells and antibodies attack and destroy germs and other foreign organism as they enter the body. The T-cell lymphocyte, also known as T-helper, T-4 or CD4, is one of the white blood cells that assist in destroying foreign proteins, an immune system response that prevents people from getting sick. Unfortunately, these are the cells HIV targets.

HIV cannot live independently. It attaches and enters the T-helper lymphocytes so that it will be able to multiply. HIV incorporates its HIV genes into the host cells and then replicates within the T-helper lymphocytes. When the newly-formed viruses break out of their cells, they continue the cycle by infecting more T-helper lymphocytes.

At some point, the body's own defenses contribute to the problem, as the immune system tries to overcome the infection by producing additional helper cells, providing yet more hosts for the virus. Eventually the system can no longer produce enough white blood cells to ward off other infections.

When the disease progresses from HIV infection to full-blown AIDS, it is because the number of T-cells has dropped to dangerous levels. AIDS is heralded by a total lymphocyte count of less than 500/mm$^3$ and a dangerously low T-cell count of below 200. With the immune system so depleted, the body becomes highly vulnerable to opportunistic diseases. As the term suggests, these are infections and other diseases that seize the opportunity presented by a weakened defense system. They commonly include herpes simplex infection and other herpes conditions such as shingles and the oral yeast infection, thrush; Kaposi's sarcoma, characterized by the dark lesions; CKV retinitis, a herpes virus that can bring blindness; meningitis, an infection of the spinal cord and brain; cervical cancer; and a formerly rare type of pneumonia.

The Department of Health & Human Services ("DHHS") has issued guidelines recommending certain antiretroviral agents for treatment of established HIV infection. The DHHS panel recommended that all patients with less than 500 CD4 T cells/mm, and a viral load greater than 10,000 (bDNA) or 20,000 (RT-PCR) copies of HIV RNA/ml, of plasma should be offered antiviral therapy. The use of various combinations of antiretroviral agents represents the current state of the art and significant benefits have been observed in many cases although the long term results remain to be established. The patients presently must adhere to complex dosage regimens and tolerate significant drug side effects and adverse reactions.

SUMMARY OF INVENTION

In brief, this invention comprises the method of raising the T-cell count in an HIV positive patient having a depressed T-cell count by orally administering an effective amount of a composition containing a precipitated material obtained by treating whole h-man blood obtained from HIV positive patients or white cells separated from whole human blood from HIV positive patients with a cold aqueous solution of carbon dioxide, heating to evolve carbon dioxide gas, allowing a precipitate to form, and collecting and drying the precipitate.

The invention further comprehends a precipitated composition obtained by treating whole human blood obtained from HIV positive patients or white cells separated from whole human blood from HIV positive patients with a cold aqueous solution of carbon dioxide, heating to evolve carbon dioxide gas, allowing a precipitate to form, and collecting and drying the precipitate.

Still further, this invention includes a method of obtaining a composition effective in raising the T-cell count in an HIV positive patient which comprises obtaining whole human blood from HIV positive patients or white cells separated from whole human blood from HIV positive patients, contacting with a cold aqueous solution of carbon dioxide, heating to evolve carbon dioxide gas, allowing a precipitate to form, and collecting and drying the precipitate.

Preferably, the cold (around 5 to 10° C.), aqueous solution of carbon dioxide contains an alkali or alkaline earth bicarbonate such as sodium, calcium or magnesium bicarbonate. The "cold" carbon dioxide-containing solution is less than room temperature (about 20° C.) but above 0° C. Normally, the solution is at or near saturation with carbon dioxide.

The cold solution containing carbon dioxide is combined with the whole blood or separated white cells. The resulting mixture should have a pH close to 7, i.e., pH about 6 to about 8. The pH can be adjusted as necessary to the desired pH 7 by adding a small amount of mineral acid such as hydrochloric acid to the cold carbon dioxide solution, to the blood, or to the mixture of the two.

The carbon dioxide solution and the blood are mixed at a volume ratio which does not cool the blood to the extent that causes coagulation. Typically, the carbon dioxide solution to blood volume ratio is from about 1 to 1 to about 1 to 5.

The mixture is heated to at least about 30° C. up to about 95° C. to evolve carbon dioxide gas and then the mixture is allowed to cool. Normally, heating is continued until all or most of the dissolved carbon dioxide has been driven off. A precipitate is formed which is collected and dried.

DESCRIPTION OF PREFERRED EMBODIMENTS

The active agent is prepared by obtaining whole blood samples from about 10-20 AIDS patients (about 100-200 cc per patient), that is, patients who are HIV positive. It is not necessary to have an equal amount of blood from each patient. Alternatively, the HIV virus can be cultivated in blood in which case the inoculated blood can then be processed and used as described elsewhere herein. However, normally a pooled sample of blood collected from HIV positive patients is used.

The pooled blood sample is placed in a first chamber. Distilled water, carbon dioxide gas and calcium bicarbonate (or magnesium bicarbonate or sodium bicarbonate) are charged to a separate closed chamber, provided with an agitator, which is cooled. Cold contents from the second chamber are added to a third chamber fitted with an ultrasonic homogenizer. Pooled blood from the first chamber is added to the third chamber. The temperature is raised to about 80-90° C. in the homogenizer chamber. The homogenizer chamber is operated at about 30,000 rpm for about 30-45 minutes. A mechanical, high speed agitator can be used in lieu of an ultrasonic homogenizer.

Carbon dioxide gas is evolved which is exhausted to the atmosphere.

The liquid aqueous contents in the homogenizer chamber are then allowed to cool and a solid precipitate forms.

The solids in the homogenizer chamber are collected on filter paper, #42 or #45. The filtrate is washed 2-4 times with distilled water. The filtrate is oven dried at about 80° C. for 8 hours. The powdered filtrate can be ground finer in a grinder.

The resulting product is a fine powder having an average particle size of smaller than 10 microns. The fine powder is sterilized at about 120° C. at 15 psig for 1 hour following the procedure for aseptic powders defined by the United States Pharmacopeia (US) under the topic of Sterility Tests.

The powdered precipitate can then be compounded with conventional fillers such as alfalfa, sunflower seed oil, wheatgrass powder, starch, lactose and vitamins, and compressed into an approximately 800 mg tablet of which 30 mg is the precipitated material of this invention. The tablets should be stored at or around room temperature. The use of fillers is not mandatory.

This 800 mg tablet is preferably orally administered 3 times daily after meals to patients suffering from AIDS accompanied by significantly depressed CD-4 levels. Those Skilled in the art can vary the dosage to suit the patient response but generally an effective dose, based on the weight of the precipitated material, is from about 20 mg to about 500 mg per day, and more preferably from about 50 to 250 mg per day.

The therapy has been found to significantly raise the CD-4 and CD-8 level in such patients.

DESCRIPTION OF THE DRAWING

The drawing shows in schematic form the apparatus used to treat the pooled blood according to this invention.

Unit 1 is a schematic diagram illustrating the apparatus used in the production of carbon dioxide dissolved in water. Unit 2 is a schematic diagram illustrating the container for the liquid blood. Connecting lines 3 and 4 are explained below. Chamber 5 is an illustration of the apparatus used for the reaction under controlled conditions of temperature and time. Chamber 5 is provided with an ultrasonic homogenizer or mechanical agitator 6.

EXAMPLE 1

Figure 1:
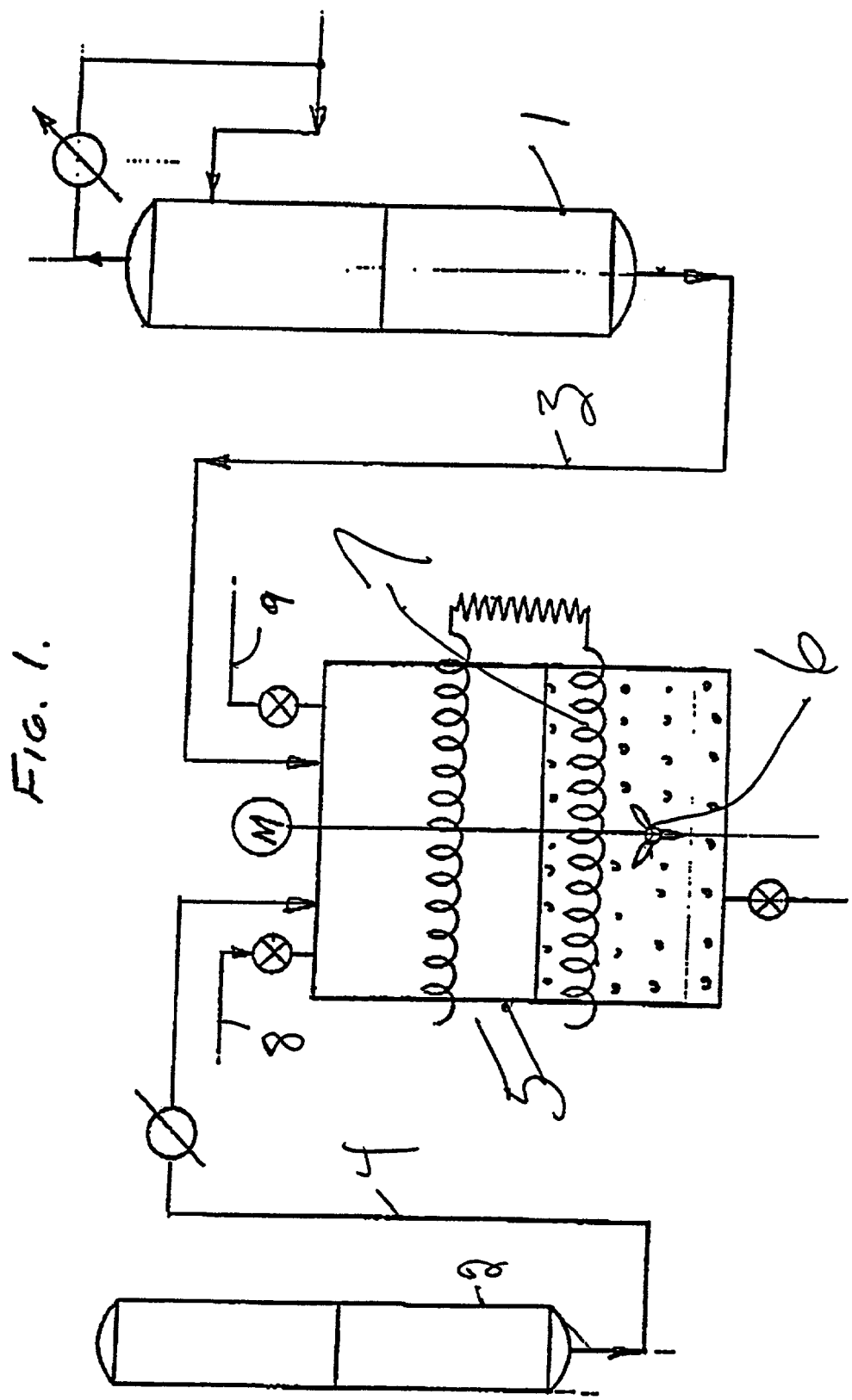

In Unit 1, pure carbon dioxide gas is mixed with 10 liter of purified water and calcium bicarbonate for 1 hour with an agitator rotation of 30 rpm, pressure of 5 lbs. per sq. in. and the temperature between 5 to 10 degree Celsius. The solution is essentially saturated with dissolved carbon dioxide. This solution is adjusted to a pH slightly above 7 by manipulation of the amount of the calcium bicarbonate added. The low temperature promotes the absorption of gas into the water. In Unit 2, a pooled blood sample from AIDS patients, about 10 patients, is introduced to provide a blood volume of about 500 cc. Unit 2 initially is at room temperature. The cold liquid containing dissolved $CO_2$ is pumped via line 3 to Chamber 5. The contents of Unit 2 are pumped via line 4 to Chamber 5 to provide a volume ratio of 1:2 ($CO_2$ solution to blood). The Chamber 5 measures 12×12×16 inches and is made of stainless steel lined with glass. As necessary, the pH of the liquid in chamber 5 is adjusted to 7 with hydrochloric acid which is added via line 8. The temperature in Chamber 5 is raised to 80-90° C. by temperature coil 7 and the ultrasonic homogenizer 6 is operated at 30,000 rpm for about 30-45 minutes. The evolved carbon dioxide gas and the ultrasonic homogenizer break the cells in the blood into very small particles. The evolved carbon dioxide gas exhausts to the atmosphere via line 9. The very small particles settle to the bottom of Chamber 5. Chamber 5 is then opened and the contents collected on filter paper #42. The precipitate will be on the filter paper. The filter paper is washed with purified water 4-5 times to remove toxic materials i.e. endotoxin. The collected precipitate is dried in a dry oven at 80 degree Celsius for 8 hours. The precipitate now is similar to clay and it is grounded into a fine powder having an average particle size under 10 microns. The ground powder is collected in a closed tight container and sterilized at 120° C. at 15 psig for about 1 hour per USP.

The sterility of the powder is confirmed by Standard USP sterility test.

The tablet used in the clinical trials had the following composition:

| | |
|---|---|
| Dry Powder as prepared in Example 1 | 30 mg |
| Nicotinamide | 15 mg |
| Iron (as ferrous fumarate) | 1 mg |
| Thiamin (as thiamin mononitrate) | 1 mg |
| Riboflavin | 1 mg |
| Pyridoxine (as pyridoxine hydrochloride) | 1 mg |
| Magnesium stearate | 11 mg |
| Starch | 370 mg |
| Lactose | 370 mg |
| Total Per Tablet | 800 mg |

This 800 mg tablet was administered orally 3 times daily following meals in the following trials.

ANALYSIS OF CLINICAL TRIALS

Fifty AIDS patients are being treated with the drug. Of these, there are 20 test cases of before and after blood tests. The "A" tests are the results prior to beginning administration of the drug. The "B" etc. tests are results subsequent to the beginning of administration of the drug. The test cases to date show that the improvement varies substantially among the patients. The average increase in CD 4 was 100 and the average increase in CD 8 was 300. The following summarizes the outcomes.

CD 4 Level 10 or less increase 35%

50 or less increase 20%

50-100 15%

100 or more increase 15%

150 or more increase 15%

CD 8 Level

Decrease 20%

50 or less increase 15%

50-300 25%

300 or more increase 20%

450 or more increase 20%

Substantial improvement is observed in about two thirds of the cases. Excellent improvement is observed in 25% of the cases. How long this improvement will occur is unknown since there are basically few tests for more than 6 months.

Of the 35% cases where CD 4 increased 10 or less, all except two had a CD 4 reading of less than 50 upon initial testing of even this group the majority showed some improvement.

Of the 35% cases where CD 8 increased 50 or less, there was no such similar finding that those acutely ill, improved the least. In fact, of the 6 cases with CD 4 less than 100, 2 decreased CD 8 but 4 increased CD 8 by over 100 and 1 increased CD 8 by over 300. Most of the people whose CD 8 decreased had increases in CD 4. (Note: in most patients it is easier to increase CD 8 than CD 4 and the initial positive result is an increase in CD 8.

After taking the drug, the muscles of the body may become sore. In many patients, within one month, there is a weight gain, a lightening of the skin, and an improvement in the energy level.

The following Lab Tests were performed in several hospitals which are the leading Government Hospitals in Thailand.

TABLE 1

TEST

| PATIENT | SEX | AGE | TEST | TEST DATE | HOSPITAL WHERE TEST WAS CONDUCTED | CD4 cells/mm | CD8 cells/mm | LYMPHO-CYTE |
|---|---|---|---|---|---|---|---|---|
| Patient No. 1 | F | 22 | A | Apr. 5, 1999 | CH | 429 | 1168 | 32.2 |
| | | | B | May 18, 1999 | CH | 510 | 1530 | 44 |
| | | | C | Jun. 28, 1999 | CH | 660 | 2430 | 49 |
| | | | D | Aug. 9, 1999 | CH | 670 | 2820 | 40 |
| Patient No. 2 | M | 27 | A | Apr. 5, 1999 | CHU | 12 | 392 | 21.9 |
| | | | B | May 17, 1999 | CH | 10 | 500 | 19 |
| | | | C | Jun. 28, 1999 | CH | 0 | 600 | 21 |
| | | | D | Aug. 9, 1999 | CH | 20 | 520 | 22 |
| Patient No. 3 | F | 24 | A | Apr. 5, 1999 | CHU | 347 | 942 | 42 |
| | | | B | May 17, 1999 | CH | 370 | 740 | 42 |
| | | | C | Jun. 14, 1999 | CH | 400 | 930 | 44 |
| Patient No. 4 | M | 28 | A | Apr. 5, 1999 | CHU | 32 | 294 | 20.6 |
| | | | B | May 17, 1999 | CH | 10 | 460 | 17 |
| Patient No. 5 | F | 28 | A | Mar. 30, 1999 | CHU | 436 | 742 | 30.8 |
| | | | B | May 28, 1999 | CHU | 399 | 1345 | 40.4 |
| | | | C | Jul. 30, 1999 | CHU | 592 | 1205 | 32.7 |
| | | | D | Oct. 1, 1999 | CHU | 647 | 1079 | 39.3 |
| Patient No. 6 | M | 35 | A | May 27, 1999 | CH | 0 | 300 | 10 |
| | | | B | Aug. 19, 1999 | CH | 0 | 690 | 23 |
| Patient No. 7 | M | 48 | A | Dec. 22, 1998 | S | 140 | 1390 | |
| | | | B | Mar. 29, 1999 | CHU | 174 | 1792 | 17.7 |
| Patient No. 8 | M | 36 | A | Oct. 13, 1998 | S | 108 | 1079 | 28 |
| | | | B | Dec. 22, 1998 | S | 130 | 1050 | |
| | | | C | Mar. 29, 1999 | CHU | 241 | 1757 | 40.8 |
| Patient No. 9 | F | 35 | A | Dec. 22, 1998 | S | 440 | 520 | |
| | | | B | Mar. 29, 1999 | CHU | 551 | 735 | 37.1 |
| Patient No. 10 | M | 33 | A | Oct. 13, 1998 | S | 17 | 645 | 29 |
| | | | B | Mar. 29, 1999 | CHU | 57 | 614 | 20.1 |
| Patient No. 11 | F | 32 | A | Oct. 13, 1998 | S | 76 | 531 | 28 |
| | | | B | Mar. 29, 1999 | CHU | 101 | 495 | 26.8 |
| Patient No. 12 | M | 30 | A | May 3, 1999 | CH | 490 | 1620 | 53 |
| | | | B | Jul. 1, 1999 | CH | 560 | 1540 | 60 |
| Patient No. 13 | F | 25 | A | May 3, 1999 | CH | 230 | 530 | 29 |
| | | | B | Jun. 3, 1999 | CH | 320 | 690 | 32 |
| Patient No. 14 | F | 36 | A | Mar. 15, 1999 | CH | 230 | 530 | 38 |
| | | | B | May 10, 1999 | CH | 210 | 1340 | 45 |
| Patient No. 15 | F | 41 | A | Mar. 2, 1999 | R | 270 | 900 | 31 |
| | | | B | Mar. 17, 1999 | R | 310 | 1070 | 29 |
| Patient No. 16 | F | 33 | A | Mar. 3, 1999 | R | 440 | 1680 | 52.8 |
| | | | B | Mar. 12, 1999 | R | 630 | 1720 | 57 |
| Patient No. 17 | M | 35 | A | Mar. 2, 1999 | R | 10 | 490 | 23.8 |
| | | | B | Mar. 12, 1999 | R | 10 | 520 | 30.4 |
| Patient No. 18 | F | 50 | A | Jun. 10, 1999 | CH | 400 | 1920 | 40 |
| | | | B | Aug. 19, 1999 | CH | 520 | 2330 | 44 |
| Patient No. 19 | M | 26 | A | Apr. 20, 1999 | CH | 0 | 240 | 10 |
| | | | B | Jun. 17, 1999 | CH | 0 | 350 | 32 |
| Patient No. 20 | F | | A | Jul. 30, 1999 | CHU | 240 | 886 | 26.5 |
| | | | B | Oct. 8, 1999 | CHU | 220 | 930 | 29.5 |

CH—Chonburi Hospital
CHU—Chulalongkom Hospital
S—Siriraj Hospital
R—Rajburi
BPL—Bangkok Pathology Laboratory
B—Bangkok General Hospital While results vary from patient to patient, the foregoing data show a general increase in CD4, CD8 and lymphocyte levels aver time, following the beginning of the administration of the drug.

Table II shows the white cell levels in the 20 patients of Table I as well an data on an additional 5 patients.

TABLE II

AIDS PATIENT'S LAB TEST AFTER TREATED WITH V-1

| Patient | Age | Test | Hospital | Date | White Cells | Lymphocyte | CD4 | CD8 |
| --- | --- | --- | --- | --- | --- | --- | --- | --- |
| Patient No. 1 | 22 | A | CH | Apr. 5, 1999 | 7,400 | 32.2 | 429 | 1168 |
|  |  | B | CH | May 18, 1999 | 6,100 | 44 | 510 | 1530 |
|  |  | C | CH | Jun. 28, 1999 | 8,400 | 49 | 660 | 2430 |
|  |  | D | CH | Aug. 9, 1999 | 11,200 | 40 | 670 | 2820 |
| Patient No. 2 | 27 | A | CHU | Apr. 5, 1999 | 5,600 | 21.9 | 12 | 392 |
|  |  | B | CH | May 17, 1999 | 6,000 | 19 | 10 | 500 |
|  |  | C | CH | Jun. 28, 1999 | 8,400 | 21 | 0 | 600 |
|  |  | D | CH | Aug. 9, 1999 | 7,200 | 42 | 20 | 520 |
| Patient No. 3 | 24 | A | CHU | Apr. 5, 1999 | 5,900 | 42 | 347 | 942 |
|  |  | B | CH | May 10, 1999 | 4,900 | 42 | 370 | 740 |
|  |  | C | CH | Jun. 14, 1999 | 5,400 | 44 | 400 | 930 |
| Patient No. 4 | 28 | A | CHU | Apr. 5, 1999 | 3,100 | 20.6 | 32 | 294 |
|  |  | B | CH | May 17, 1999 | 4,200 | 17 | 10 | 460 |
| Patient No. 5 | 28 | A | CHU | Mar. 30, 1999 | 5,240 | 30.8 | 436 | 742 |
|  |  | B | CHU | May 28, 1999 |  | 40.4 | 399 | 1345 |
|  |  | C | CHU | Jul. 30, 1999 | 6,700 | 32.7 | 592 | 1205 |
|  |  | D | CHU | Oct. 1, 1999 |  | 39.3 | 647 | 1079 |
| Patient No. 6 | 35 | A | CH | May 27, 1999 | 5,700 | 10 | 0 | 300 |
|  |  | B | CH | Aug. 19, 1999 | 4,900 | 23 | 0 | 690 |
| Patient No. 7 | 48 | A | S | Dec. 22, 1998 |  |  | 140 | 1390 |
|  |  | B | CH | Mar. 29, 1999 | 6,600 | 17.7 | 174 | 1792 |
| Patient No. 8 | 36 | A | S | Oct. 13, 1998 | 5,700 | 28 | 108 | 1079 |
|  |  | B | S | Dec. 22, 1998 |  |  | 130 | 1050 |
|  |  | C | CHU | Mar. 29, 1999 | 5,900 | 40.8 | 241 | 1757 |
| Patient No. 9 | 35 | A | S | Dec. 22, 1998 |  |  | 440 | 520 |
|  |  | B | CHU | Mar. 29, 1999 | 4,500 | 37.1 | 551 | 735 |
| Patient No. 10 | 33 | A | S | Oct. 13, 1998 | 3,300 | 28 | 17 | 645 |
|  |  | B | CHU | Mar. 29, 1999 | 4,700 | 20.1 | 57 | 614 |
| Patient No. 11 | 32 | A | S | Oct. 13, 1998 | 3,700 | 28 | 76 | 531 |
|  |  | B | CHU | Mar. 29, 1999 | 4,200 | 26.8 | 101 | 495 |
| Patient No. 12 | 30 | A | CH | May 3, 1999 | 6,800 | 53 | 490 | 1620 |
|  |  | B | CH | Jul. 1, 1999 | 7,200 | 60 | 560 | 1540 |
| Patient No. 13 | 25 | A | CH | May 3, 1999 | 5,500 | 29 | 230 | 530 |
|  |  | B | CH | Jun. 3, 1999 | 6,300 | 32 | 320 | 690 |
| Patient No. 14 | 36 | A | CH | Mar. 15, 1999 | 4,500 | 38 | 230 | 530 |
|  |  | B | CH | May 10, 1999 | 4,300 | 45 | 210 | 1340 |
| Patient No. 15 | 41 | A | R | Mar. 2, 1999 | 5,100 | 31 | 270 | 900 |
|  |  | B | R | Mar. 17, 1999 | 6,600 | 29 | 310 | 1070 |
| Patient No. 16 | 33 | A | R | Mar. 3, 1999 | 6,000 | 52.8 | 440 | 1680 |
|  |  | B | R | Mar. 12, 1999 | 5,800 | 57 | 630 | 1720 |
| Patient No. 17 | 35 | A | R | Mar. 2, 1999 | 4,600 | 23.8 | 10 | 490 |
|  |  | B | R | Mar. 12, 1999 | 3,600 | 30.4 | 10 | 520 |
| Patient No. 18 | 50 | A | CH | Jun. 10, 1999 | 7,600 | 40 | 400 | 1920 |
|  |  | B | CH | Aug. 19, 1999 | 8,400 | 44 | 520 | 2330 |
| Patient No. 19 | 26 | A | CH | Apr. 20, 1999 | 3,900 | 10 | 0 | 240 |
|  |  | B | CH | Jun. 17, 1999 |  | 32 | 0 | 350 |
| Patient No. 20 |  | A | CHU | Jul. 30, 1999 | 6,900 | 26.8 | 240 | 888 |
|  |  | B | CHU | Oct. 8, 1999 |  | 29.5 | 220 | 930 |
| Patient No. 21 | 28 | A | CH | Apr. 15, 1999 | 5,900 | 10 | 0 | 180 |
|  |  | B | CH | Jan. 10, 2000 | 22,300 | 2 | 0 | 100 |
| Patient No. 22 | 49 | A | CHU | Jul. 6, 1999 | 3,820 | 17.1 | 111 | 307 |
|  |  | B | CHU | Nov. 26, 1999 | 7,900 | 34.9 | 551 | 1516 |
| Patient No. 23 | 60 | A | RA | Nov. 6, 1998 |  |  | 175 | 437 |
|  |  | B | RA | Nov. 19, 1999 | 5,120 |  | 237 | 1163 |

TABLE II-continued

AIDS PATIENT'S LAB TEST AFTER TREATED WITH V-1

| Patient | Age | Test | Hospital | Date | White Cells | Lymphocyte | CD4 | CD8 |
|---|---|---|---|---|---|---|---|---|
| Patient No. 24 | 20 | A | SR | Jun. 24, 1999 | 5,100 | 48 | 195 | |
| | | B | V | Dec. 5, 1999 | 9,600 | 34 | 100 | |
| Patient No. 25 | 34 | A | CH | Jul. 1, 1999 | 9,400 | 350 | 1560 | |
| | | B | CH | Oct. 10, 1999 | 10,500 | 420 | 2650 | |

Hospital where test was conducted in Thailand
B—Bangkok General Hospital
CHU—Chulalonqkom Hospital
RA—Ramatibodi Hospital
CH—Chonburi Hospital
S—Siriraj Hospital
BPL—Bangkok Pathology Laboratory
R—Rajburi Hospital
SR—Srinakarin Hospital
V—Vachiraprakarn Hospital The dosage preferred is 3 times perday, half an hour after each meal.

After taking the drug, some patients feel soreness in their muscle and joints because of the stimulation of the immune system. The pain is gone in about one week. Some patients have an upset stomach but this condition disappears in 3-7 days. The drug should not be used in conjunction with anti-inflammatory drugs.

The drug has no side effects on the liver or kidney. Therefore, it can be used on a sustained basis. The duration of usage depends on the measured status of the immune system. The administration of the drug can be reduced to every other week when the CD4 rises to over 500 and it can be should be stopped when the blood test no longer shows HIV positive.

The following claims define the invention.

The invention claimed is:

1. A composition obtained by treating whole human blood obtained from HIV positive patients or white cells separated from whole human blood from HIV positive patients with a cold aqueous solution of carbon dioxide, agitating or homogenizing the solution, heating to evolve carbon dioxide gas, allowing a precipitate to form, and collecting and drying the precipitate.

2. The composition of claim 1 wherein the cold aqueous solution is at about 0° C. to about 20° C.

3. The composition of claim 1 wherein the treating is by mixing whole human blood with cold aqueous solution at a volume ratio between about 1 to 1 and about 1 to 5 and the resulting mixture has a pH of from about 6 to about 8.

4. The composition of claim 1 wherein the heating to evolve carbon dioxide is at about 30° C. to about 95° C.

5. The method of obtaining a composition effective in raising the T-cell count in an HIV positive patient having a depressed T-cell count which comprises obtaining whole human blood from HIV positive patients or white cells separated from whole human blood from HIV positive patients, contacting with a cold aqueous solution of carbon dioxide, agitating or homogenizing the solution, heating to evolve carbon dioxide gas, allowing a precipitate to form, and collecting and drying the precipitate.

6. The method of claim 5 wherein the cold aqueous solution is at about 0° to about 20° C.

7. The method of claim 5 wherein the treating is by mixing whole human blood with cold aqueous solution at a volume ratio between about 1 to 1 and about 1 to 5 and the resulting mixture has a pH of from about 6 to about 8.

8. The method of claim 5 wherein the heating to evolve carbon dioxide is at about 30° C. to about 95° C.

* * * * *